United States Patent
Bonte et al.

(10) Patent No.: US 9,456,627 B2
(45) Date of Patent: Oct. 4, 2016

(54) PROCESS FOR ISOLATING SIALIC ACID CONTAINING OLIGOSACCHARIDES, AND THE COMPOSITIONS CONTAINING SIALIC ACID CONTAINING OLIGOSACCHARIDES OBTAINABLE THEREBY

(75) Inventors: Alfred Willy Bonte, Neede (NL); Gijsbert Klarenbeek, Ommen (NL); Marcus Johannes Aloysius Becker, Nijverdal (NL)

(73) Assignee: FRIESLAND BRANDS B.V., Amersfoort (NL)

( * ) Notice: Subject to any disclaimer, the term of this patent is extended or adjusted under 35 U.S.C. 154(b) by 213 days.

(21) Appl. No.: 12/921,474

(22) PCT Filed: Mar. 13, 2009

(86) PCT No.: PCT/NL2009/050124
§ 371 (c)(1),
(2), (4) Date: Nov. 5, 2010

(87) PCT Pub. No.: WO2009/113861
PCT Pub. Date: Sep. 17, 2009

(65) Prior Publication Data
US 2011/0098244 A1    Apr. 28, 2011

(30) Foreign Application Priority Data
Mar. 14, 2008    (NL) .................................. 2001377

(51) Int. Cl.
| A23L 1/305 | (2006.01) |
| C07H 1/08 | (2006.01) |
| C07H 1/06 | (2006.01) |
| A23L 1/29 | (2006.01) |
| A23C 9/146 | (2006.01) |
| A23C 9/20 | (2006.01) |

(52) U.S. Cl.
CPC .............. *A23L 1/296* (2013.01); *A23C 9/1465* (2013.01); *A23C 9/203* (2013.01); *A23L 1/3056* (2013.01); *C07H 1/08* (2013.01); *A23V 2002/00* (2013.01)

(58) Field of Classification Search
CPC ....... C07H 1/06; C07H 1/00; C07K 2317/41
USPC .................................................. 536/127, 124
See application file for complete search history.

(56) References Cited

U.S. PATENT DOCUMENTS

| 5,118,516 | A |   | 6/1992 | Shimatani et al. |
| 5,576,040 | A | * | 11/1996 | Moller et al. .................. 426/271 |
| 5,714,075 | A |   | 2/1998 | Brian et al. |
| 6,288,222 | B1 |   | 9/2001 | Roth et al. |
| 6,323,008 | B1 | * | 11/2001 | Pelletier et al. ................ 435/84 |
| 6,623,954 | B1 |   | 9/2003 | Spade et al. |
| 2007/0104700 | A1 |   | 5/2007 | Garcia-Rodenas et al. |
| 2008/0003330 | A1 |   | 1/2008 | Rueda et al. |

FOREIGN PATENT DOCUMENTS

| EP |     474410 | B1 | * | 10/1996 |
| EP |    1008303 | A1 |   | 6/2000 |
| JP |   59184197 |    |   | 10/1984 |
| JP | 2001206848 | A  | * | 7/2001 |
| WO | WO 03102205 | A1 | * | 12/2003 |
| WO | 2007051475 | A1 |   | 5/2007 |

OTHER PUBLICATIONS

Kudo et al, JP 2003230881 A (Derwent Abstract), Aug. 19, 2003.*
Idota et al., "Changes in the Sialyllactose Content of Human Milk During Lactation", XP002293321, Abstract, 1900.
Database WPI Week 199843, Thomson Scientific, London, GB; XP002505046 and JP 02802654 B2, Abstract, 1998.

* cited by examiner

*Primary Examiner* — Patrick Lewis
*Assistant Examiner* — Everett White
(74) *Attorney, Agent, or Firm* — Hoffman & Baron, LLP

(57) ABSTRACT

The invention relates to a process for isolating sialic acid containing oligosaccharides and in particular sialyllactose from a milk stream and especially from a whey stream. The process yields a product having a high content of sialyllactose and a low content of phosphorus compounds. This product is highly suitable to be included in infant foods.

13 Claims, 1 Drawing Sheet

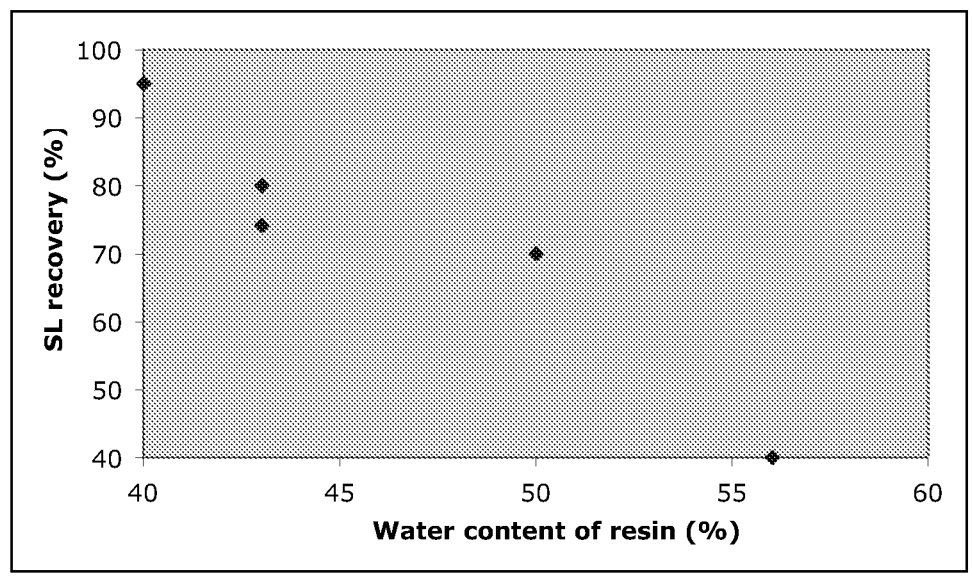

PROCESS FOR ISOLATING SIALIC ACID CONTAINING OLIGOSACCHARIDES, AND THE COMPOSITIONS CONTAINING SIALIC ACID CONTAINING OLIGOSACCHARIDES OBTAINABLE THEREBY

This application is the U.S. National Phase of, and Applicants claims priority from, International Application Number PCT/NL2009/050124 filed 13 Mar. 2009 and Netherlands Patent Application No. NL 2001377 filed 14 Mar. 2008, each of which are incorporated herein by reference.

BACKGROUND OF THE INVENTION

The invention relates to a process for isolating oligosaccharides which contain a substituent derived from sialic acid (hereinafter: sialic acid containing oligosaccharides) and preferably sialyllactose containing compositions and especially such compositions in which the ratio between sialic acid containing oligosaccharides and phosphorus, and preferably the ratio between sialyllactose and phosphorus, is relatively high. In addition, the invention relates to the obtainable and obtained compositions and the use of those compositions, in especially infant foods.

Sialyllactose is a milk oligosaccharide which occurs in milk of mammals. It is known that the concentration of this milk oligosaccharide in, for instance, cow's milk is very low; in human milk the sialyllactose occurs in concentrations which in an absolute sense are considerably higher.

Sialyllactose has a number of important functionalities. Thus, it is known that it possesses a prebiotic activity, and bifidogenic effects have been described. In addition, the sialyllactose is an anti-adhesive, allowing it to play an important role in inhibiting or preventing intestinal infections by binding pathogenic bacteria and/or viruses and/or toxins being released, so that colonization on the one hand and the effect of the toxins on the other hand can be prevented. Also, it has been described that sialyllactose can promote brain growth in infants.

Such positive effects are also attributed to other sialic acid containing oligosaccharides.

Since, as a rule, the aim is to make infant and baby foods resemble human milk as much as possible, there is a need (especially with infant milk formulators) to enrich such foods with sialic acid containing oligosaccharides and preferably with sialyllactose. This is also one of the objects of the present invention.

To obtain sialic acid containing oligosaccharides in general and sialyllactose in particular, different processes have already been proposed in the prior art. A large number of those processes are aimed at the enzymatic preparation of sialyl group containing compounds such as sialyllactose, and especially using enzymes obtained from genetically modified organisms, whereby, with for instance a sialidase, sialyl transferase and/or neuraminidase, the desired sialyl group containing oligosaccharides can be formed and which can then be isolated through downstream processing.

In addition, a number of processes are known whereby sialic acid and sialyllactose are isolated from milk through combinations of chromatographic techniques and/or membrane filtration techniques.

An important disadvantage of the existing methods of recovering sialyloligosaccharides and sialic acid is that they yield the desired compounds in relatively low contents, or concentrations, while moreover in these methods a high phosphorus content is present in the sialyloligosaccharide composition. Publications are known in which it is described that foods that are phosphorylated to a high degree are digested poorly, at least less well, may adversely affect the calcium and iron absorption into the system, and generally complex with bivalent cations that are necessary for usual physiological processes in the gastrointestinal tract, while moreover the action of certain enzymes in the gastrointestinal tract may be inhibited. Especially with infant and baby food, this can lead to problems.

In an infant milk formula, the amount of phosphorus is determined especially by the protein additions. Extra phosphorus additions through other ingredients are not recommended and even advised against. Also for this reason, the provision is contemplated of sialic acid containing oligosaccharide compositions and in particular sialyllactose containing compositions in which the ratio between sialyl groups and phosphorus is as high as possible.

An object of the process according to the present invention is to provide a process in which separation techniques are used that lead to a product with relatively few phosphorus compounds in relation to the sialic acid containing oligosaccharide. This makes the product highly suitable to be used in infant foods.

Such a process is also described in U.S. Pat. No. 6,623,954. In this publication a process is described in which a dairy stream containing lactose and sialyloligosaccharides is contacted with phytase and a β-galactosidase, after which the dairy stream is subjected to nanofiltration and/or ultrafiltration, whereby the desired sialyllactose is retained in the peptide fraction; after a denaturation step and a subsequent microfiltration, a sialyllactose fraction is obtained. Optionally, before the step in which the dairy stream is contacted with the enzymes, a step may be conducted in which the positively charged materials are removed, for instance with a cation exchanger or with reverse osmosis.

An important disadvantage of this process is that as a result of the membranes used an important part of the sialyloligosaccharides including sialyllactose cannot be recovered and that it may take a long time before a product is obtained that satisfies a low ratio of phosphorus to sialyloligosaccharides.

The present invention is carried out without it being necessary to use enzymes to obtain a low phosphorus content. Further, the invention makes it possible to recover sialyloligosaccharides with a high degree of efficiency (high yield) and selectivity (high purity).

BRIEF DESCRIPTION OF THE DRAWING

FIG. 1: The relation between the moisture content of an anion exchange resin and the obtained sialyllactose (SL) recovery.

DESCRIPTION OF THE INVENTION

To this end, the invention in a first aspect concerns a process for isolating sialyllactose from a defatted, and preferably protein free, milk stream, wherein the milk stream is subjected to an anion exchange step utilizing an anion exchange resin, preferably in the free base form. The resin is further characterized by a moisture content of 30-48%. In the next step, the sialyllactose is bound to an anion exchange resin, preferably of the macroporous or gel type. The macroporous or gel type anion exchange resin preferably has a moisture content higher than 45% and most preferably between 50 and 70%.

The first type of anion exchange resin, characterized by the moisture content of 30-48%, is preferably a gel type anion exchanger which desalts the milk stream, though without thereby binding the sialyl group containing oligosaccharides and in particular the sialyllactose, which oligosaccharides are also present in salt form. In other words, this involves an anion exchange resin which has selectivity for negatively charged minerals, but not for sialyllactose. To this end, it is necessary that the moisture content, that is, the water content, is not greater than 48%, and preferably not greater than 45%. At moisture contents lower than 35%, and more so at moisture contents lower than 30%, the desalting capacity starts to become too low to yield an effective process.

The moisture content in the anion exchanger is determined in the following manner: prior to measurement of the moisture content of the resin, adhering water is removed, for instance by wrapping the resin in a cloth and then subjecting it to centrifugation (centrifuge: 30 cm diameter; 3,000 rpm); the resin is then weighed, for instance in a weighing bottle; after which the resin is dried for 4 hours at a constant temperature of 105° C.; the resin is then cooled down in an exsiccator for 30 minutes; after which in turn the weight of the dry resin is determined; the moisture percentage (wt. %)=[(weight loss after drying (g))/(weight of the wet resin)] *100%.

Through this desalting, an important part of the negatively charged ions is removed without substantial amounts of sialyllactose (despite the negative charge) being thereby removed.

The anion exchange resin mentioned is preferably and usually in the free base form (hydroxide form) because this results in a greatest possible desalting capacity. Suitable anion exchange resins are strongly cross-linked polystyrene-divinylbenzene gels, such as Diaion SA20A, Diaion WA20A (ex Mitsubishi).

The inventors have found the moisture content of the anion exchange resin used for desalting to be of importance for the removal of ash (negatively charged minerals) on the one hand and the non-binding of sialyllactose (SL) on the other hand. For this purpose, a large number of resins were tested under controlled conditions.

| Supplier | Resin | Water content (%) | SL recovery |
|---|---|---|---|
| Mitsubishi | DIAION SA10A | 43-47 | 80 |
| Mitsubishi | DIAION SA20A | 38-44 | 97 |
| Applexion | XA4013 | 50-60 | 70 |
| Applexion | XA4023 | 40-48 | 95 |
| Applexion | XA3112 | 56-64 | 40 |
| DOW | Dowex 1-X8 | 43-48 | 74 |
| DOW | Marathon A2 | 50-60 | 70 |

In these determinations, the controlled conditions were as follows:

A setup is made, consisting of two columns. The first column contains 15 ml of Marathon C resin (ex Dow; cation exchanger H$^+$ form), the second column contains the anion exchanger to be examined in the hydroxide form. The columns are tested by passing over softened NF concentrate (see also Example 1) at a rate of 0.5 ml/minute. After approximately 5 bed volumes have been applied, the recovery of SL can be determined. The relation between the moisture content and the obtained SL recovery is further plotted in FIG. 1.

In order not to obtain any loss of sialyllactose during this process, the pH of the obtained product is preferably between pH=3 and pH=9. To accomplish this, in a preferred embodiment, also the cations present (especially sodium and potassium) are removed with a cation exchange resin. The cation exchange resin is in the H$^+$ form. In a preferred configuration, first the cations are removed and then the anions.

After the desalting step, the demineralized milk stream is contacted with preferably a macroporous or gel type anion exchange resin, which is capable of capturing and binding sialyllactose. Theoretically, sialyllactose can be bound to any anion exchange resin, because the mineral salts are presently removed. To enhance effectiveness, preferably, the moisture content of the macroporous or gel type anion exchange resin is greater than 45% and more preferably it is between 50 and 70%. In such resins, larger pores are present than in the anion exchanger used in the preceding step. The sialyllactose allows of simple elution from the anion exchange resin with a small volume of a common salt or other salt solution, preferably an acid salt solution.

The eluate obtained is preferably neutralized with the aid of diluted acid, for instance hydrochloric acid, to a pH of between pH=3 and pH=9. Preferably, the pH of the end product is pH=6.5.

Examples of suitable anion exchangers for binding sialyllactose are:

| | water content |
|---|---|
| DIAION SA21A | 55-65%; |
| DIAION HPA25 | 58-68%; |
| DIAION WA10 | 63-69%; |
| DOWEX 1X4 | 55-63%; |
| DOWEX Marathon A | 60-72%. |

To adsorb sialyllactose, the resins should preferably be in the free base form. The temperature of the anion exchange step is preferably lower than 20° C. and more preferably lower than 10° C.

After the elution of sialyllactose from the anion exchange resin, a product can be obtained with a sialyllactose content of more than 4 wt. %, preferably more than 5 wt. %, most preferably more than 8 wt. %, for instance approximately 10%, based on the dry matter. Incidentally, the sialyllactose content based on dry matter can be further increased utilizing conventional techniques, such as for instance nanofiltration. In general, the sialyllactose content of the product obtained according to the process of the invention varies between 8 and 15%, although it is still possible to achieve still higher concentrations. One method of arriving at still higher concentrations is to flush more lactose away from the anion exchange resin. This can be accomplished by prolonging the flushing of the column with water, prior to the elution with salt.

The milk stream to be treated with the anion exchange resin contains no fat, at least less than 0.5, more preferably less than 0.2 and most preferably less than 0.1 wt. % of fat. It is greatly preferred for this milk fraction to be free of protein. Especially of advantage is starting from a whey stream and, more preferably still, from a whey permeate. Incidentally, it is not critical from what mammal the milk originates, and good results can be obtained when the starting material is cow's milk, sheep milk, goat milk, camel milk or horse milk.

In a preferred embodiment, the milk stream, and more preferably the whey stream, and most preferably the whey permeate stream, before being subjected to either of the two anion exchange steps, is softened. In this softening step, polyvalent ions, for instance calcium ions and phosphate ions, are removed from the milk stream. This can for instance be done by precipitating the ions concerned; or by exchanging these ions for, for instance, sodium and chloride ions by ion exchange steps. This embodiment is illustrated below in Example 1.

In a further preferred embodiment, the invention concerns a process wherein the softened milk stream, before being subjected to either of the two anion exchange steps, is subjected to nanofiltration, such that a concentrate is formed having, in absolute amount, a lower (compared with the starting stream before nanofiltration) number of single ions, and non-protein nitrogen compounds, and especially urea. This embodiment is illustrated in Example 2.

By use of the process according to the invention, a composition with sialyllactose therein is obtained having a high weight ratio of sialyllactose to phosphorus. As a rule, this ratio according to the invention is at least greater than or equal to 6, preferably greater than or equal to 7, more preferably greater than or equal to 9, and more preferably still greater than or equal to 10.

For calculating this ratio, the content of sialyllactose is defined as being the sum of the content of 3'-SL and 6'-SL per unit weight of product.

In particular, the concentration of sialyllactose is determined with the aid of a chromatographic technique on an anion exchanger (PA-1 column, Dionex). The sialyllactose is detected with the aid of a pulsed amperometric detector. The sialyllactose content is calculated as the sum of the content of 3'-sialyllactose and 6'-sialyllactose.

The phosphorus content is defined as the total content of phosphorus (after destruction with nitric acid) per unit weight of product according to "AOAC official method 973.55 (analysis of phosphorus in water)".

Next, the ratio between sialyllactose and phosphorus can be calculated.

Incidentally, the known processes that isolate sialyllactose from milk as a rule result in products in which the sialyllactose/phosphorus ratio is lower than 5.

According to the invention, in the softening step about 50-60% of the phosphorus compounds are removed; in the step where the anion exchanger with a moisture content between 30 and 48% is used, some 30% of the phosphorus compounds are removed; and in the step where the anion exchanger of preferably the macroporous or gel type is used, another approximate 10% of the phosphorus compounds are removed.

In a second aspect, the invention relates to a composition containing sialic acid-containing oligosaccharides or acid oligosaccharides, preferably containing sialyllactose, obtainable by the use of the process according to the invention, having a sialyllactose content based on dry matter of at least 4 wt. %, and having a sialyllactose/phosphorus weight ratio greater than 6. Present in this composition, besides sialyllactose, are also: sialic acid, lactose, non-protein nitrogen compounds, and possibly protein.

Preferred embodiments have the above-described contents and weight ratios.

In a third aspect, the invention concerns the use of the composition of the invention containing sialic acid-containing oligosaccharides and especially the sialyllactose, in infant food, and especially such that sialyllactose contents are obtained that correspond to the contents thereof in human milk.

This does not mean, for that matter, that the sialyllactose could not be used in other applications, such as clinical and enteral foods or, for instance, for cosmetic application as an ingredient in skin conditioners, related to modulating pigment activity and/or reduction of skin damages.

Presently, the present invention will be elucidated in and by the following non-limiting examples. Where in the Examples or in the above text percents or ppm's are used, these are—unless otherwise stated—respectively percents by weight and parts per million by weight of a constituent based on the weight of the composition incorporating that constituent.

Example 1

A whey permeate stream having a dry matter content of 6.66% was passed in succession over an anion exchange resin (XA3112 (ex Applexion); in chloride form) and over a cation exchange resin (XA 2033 (ex Applexion); in sodium form). In this process, depending on the applied loading, an amount of phosphate and calcium was found to be exchanged for chloride and sodium ions, respectively. When about 25 bed volumes (BV's) of whey permeate are applied, about 90% of the calcium ions present and about 50-60% of the phosphate present were found to be removed. Experimental data of a typical permeate softening are summarized in Table 1.

TABLE 1

Experimental data on whey permeate softening
(Volume cation exchange resin = 35 l, volume anion exchange resin = 35 l)

|  | Whey permeate | Softened product |
|---|---|---|
| Volume (l) | 800 | 820 |
| Dry matter (%) | 6.66 | 6.37 |
| Sialyllactose (SL) (ppm) | 103 | 102 |
| Ash (%) | 0.63 | 0.58 |
| Phosphate (ppm) | 470 | 250 |
| Calcium (ppm) | 460 | 0.3 |
| Sodium (ppm) | 520 | 2300 |
| Chloride (ppm) | 1500 | 2800 |

Example 2

The product obtained in Example 1 was concentrated by the use of nanofiltration. Nanofiltration was carried out with an NF-2540 membrane (DOW). During the filtration process a pressure across the membrane in the range of 20-25 bar was used. The concentrate was obtained through continuous recirculation of the starting material over the membrane. As a result, the dry matter content in the concentrate increased. Thus, the dry matter content of the concentrate could be set at >15%, while it was also possible to stop filtration when a dry matter content of 20% was reached. In this way, a large part of the minerals present was removed. The experimental results of a typical nanofiltration step are summarized in Table 2.

TABLE 2

|  | Softened product | NF concentrate |
|---|---|---|
| Volume (l) | 820 | 242 |
| Dry matter (%) | 6.37 | 17.31 |
| Ash (%) | 0.58 | 0.71 |
| SL (ppm) | 102 | 314 |

Example 3

Of the product obtained in Example 2, 200 liters with a dry matter content of about 20% were successively passed over the following columns.

Column 1 contained 25 liters of cation exchanger (Applexion 748H).

Column 2 contained 25 liters of anion exchanger (DIAION SA20).

The resins were brought into H$^+$ and OH$^-$ form, respectively. The flow rate at which the product was applied was 100-125l/hour. Excluding "sweet-on" and including "sweet-off", about 220-230 liters of product could be obtained.

The thus obtained product was completely desalted and still contained virtually all sialyllactose. In general, the yield was found to be greater than 90%. A typical result of this step is summarized in Table 3.

TABLE 3

Typical result desalting of NF concentrate

|  | NF concentrate | Product |
|---|---|---|
| Volume (l) | 200 | 220 |
| Dry matter (%) | 19.36 | 16.56 |
| Ash (%) | 0.74 | 0.03 |
| SL (ppm) | 380 | 325 |

Example 4

In the next step, the sialyllactose present in the product of Example 3 was bound to a different anion exchanger. To this end, the obtained product (220 l) was passed over an anion exchanger (column volume=5 l, resin=XA900H, ex Applexion). As a result of this treatment, substantially all of the sialyllactose present was bound onto the anion exchange resin.

After flushing of the column, the bound SL could be recovered by eluting the anion exchanger with an amount of salt (40 l; 0.2M NaCl). During elution the pH was neutralized using hydrochloric acid to about pH=6.5. A typical result is summarized in Table 4:

TABLE 4

Typical results of capture and subsequent elution of SL from the anion exchange resin.

|  | Demineralization | SL-free product | SL product |
|---|---|---|---|
| Volume (l) | 220 | 230 | 40 |
| Dry matter (%) | 16.56 | 15.26 | 1.23 |
| Ash (%) | 0.03 | 0.019 | 0.26 |
| SL (ppm) | 325 | 5 | 1520 |
| P* (ppm) | 105 | 3 | 125 |

*phosphorus content according to AOAC 973.55

The invention claimed is:

1. A process for isolating sialyllactose containing compositions enriched in sialyllactose from a defatted milk stream, wherein the milk stream is subjected to a first anion exchange step utilizing an anion exchange resin in free base form, and having a moisture content of 30-48%; followed by a second anion exchange step to bind sialyllactose; and subsequent recovery of the bound sialyllactose from the second anion exchange, wherein the obtained sialyllactose containing compositions enriched in sialyllactose have a sialyllactose to phosphorus ratio that is greater than or equal to 6.

2. A process according to claim 1, wherein the second anion exchange resin has a moisture content higher than 45%.

3. A process according to claim 1, wherein the milk stream is a whey stream.

4. A process according to claim 1, wherein the milk stream, before being subjected to either of the two anion exchange steps, is softened.

5. A process according to claim 4, wherein the softening is carried out by precipitating calcium and phosphate ions.

6. A process according to claim 4, wherein the milk stream, before being subjected to either of the two anion exchange steps, is subjected to nanofiltration, such that a concentrate is formed having, in absolute amount, a lower number of single ions, and non-protein nitrogen compounds.

7. The process according to claim 1, wherein the milk stream is protein-free.

8. The process according to claim 1, wherein the second anion exchange step is accomplished using a macroporous or gel type anion exchange resin.

9. A process according to claim 1, wherein the second anion exchange resin has a moisture content between 50 and 70%.

10. A process according to claim 1, wherein the milk stream is a whey permeate.

11. A process according to claim 1, wherein the milk stream is softened utilizing ion exchangers in sodium/chloride form.

12. A process according to claim 1, wherein said sialyllactose containing compositions have a sialyllactose content of 5 to 15 wt. %.

13. A process according to claim 1, wherein the process is carried out without using enzymes to obtain a low phosphorus content.

* * * * *